United States Patent [19]

Osborne

[11] Patent Number: 4,548,206
[45] Date of Patent: Oct. 22, 1985

[54] CATHETER WIRE GUIDE WITH MOVABLE MANDRIL

[75] Inventor: Thomas A. Osborne, Bloomington, Ind.

[73] Assignee: Cook, Incorporated, Bloomington, Ind.

[21] Appl. No.: 515,636

[22] Filed: Jul. 21, 1983

[51] Int. Cl.⁴ .............................................. A61B 5/02
[52] U.S. Cl. .................................................... 128/772
[58] Field of Search ..................... 128/772, 348.1, 785, 128/356, 786, 657, 328; 604/164, 170, 282

[56] References Cited

U.S. PATENT DOCUMENTS

| | | | |
|---|---|---|---|
| 1,920,006 | 7/1933 | Dozier | 604/170 |
| 3,452,742 | 7/1969 | Muller | 128/772 |
| 3,547,103 | 12/1970 | Cook | 128/772 |
| 3,731,671 | 5/1973 | Mageoh | 128/772 |
| 3,749,086 | 7/1973 | Kline et al. | 128/772 |
| 3,757,768 | 9/1973 | Kline | 604/170 X |
| 3,789,841 | 2/1974 | Antoskiw | 128/772 |
| 3,841,308 | 10/1974 | Tate | 128/772 |
| 3,922,378 | 11/1975 | Kline | 128/772 X |
| 3,973,556 | 8/1976 | Fleishhacker et al. | 128/772 |
| 4,003,369 | 1/1977 | Heilman et al. | 128/772 |
| 4,080,706 | 3/1978 | Heilman et al. | 128/772 X |
| 4,215,703 | 8/1980 | Willson | 128/772 |
| 4,285,347 | 8/1981 | Hess | 128/785 |

Primary Examiner—Edward M. Coren
Attorney, Agent, or Firm—Woodard, Weikart, Emhardt & Naughton

[57] ABSTRACT

A catheter wire guide having an axially movable mandril with a tapered tip for permitting the flexibility of the distal tip of the wire guide to be varied. The mandril is coated with a lubricating material, such as Teflon, for facilitating the smooth movement of the mandril within the wire guide.

5 Claims, 5 Drawing Figures

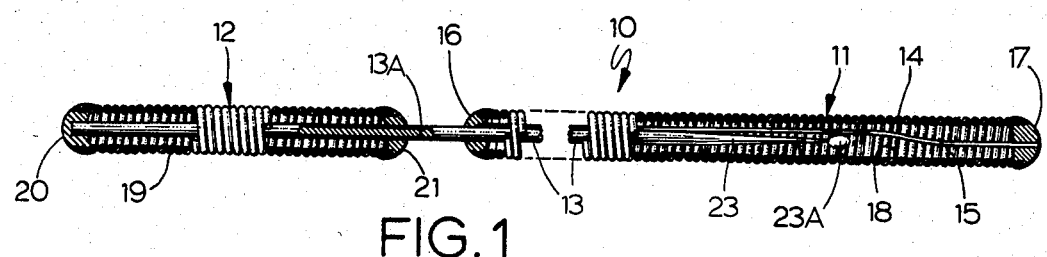
FIG. 1
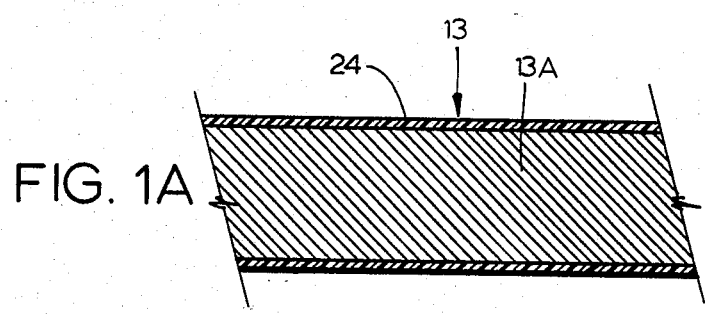
FIG. 1A
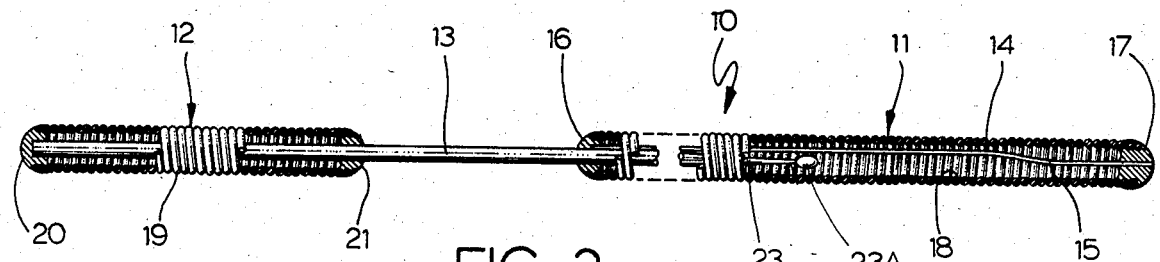
FIG. 2
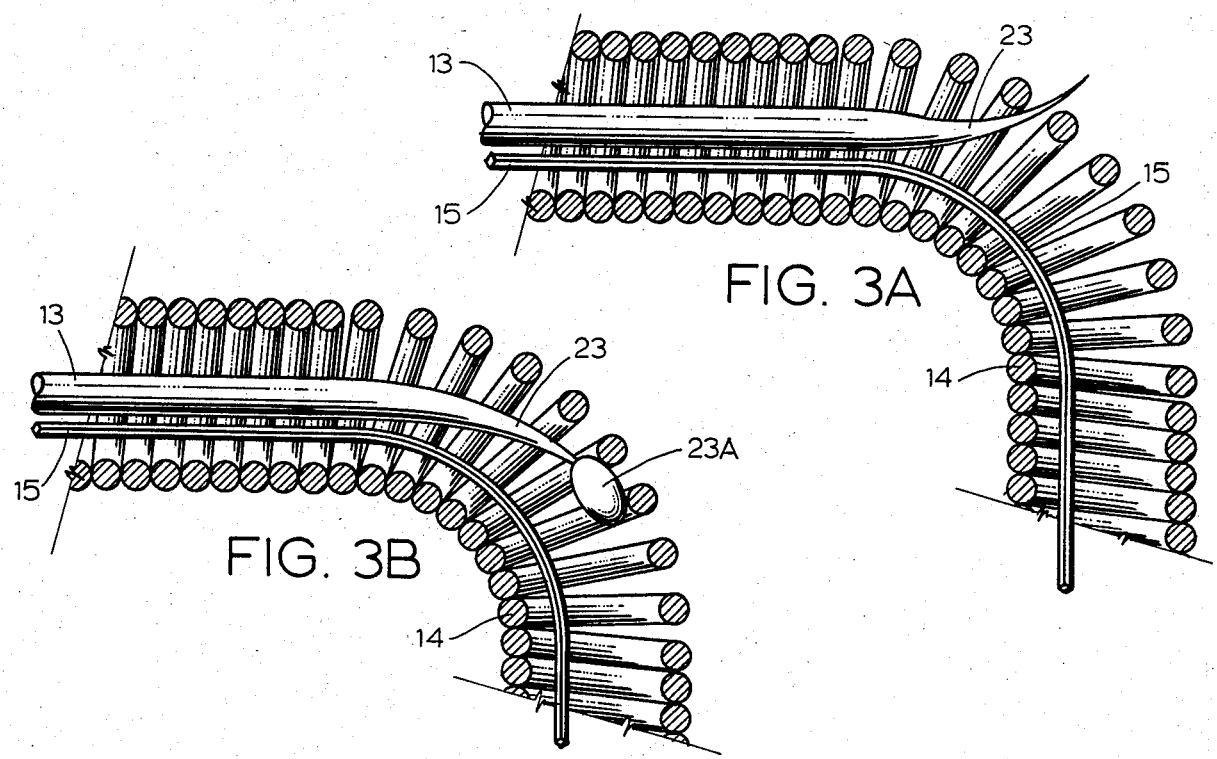
FIG. 3A
FIG. 3B

CATHETER WIRE GUIDE WITH MOVABLE MANDRIL

BACKGROUND OF THE INVENTION

The present invention relates to a wire guide for use in performing a catheterization and, more particularly to a coil spring wire guide having a movable mandril.

As described herein, the purpose of a wire guide is to aid the insertion and placement of a flexible catheter within a body blood vessel. The wire guide may be used in a procedure known as catheterization by the percutaneous entry or Seldinger technique. Employing this technique, a needle assembly including a stylet and a sharp pointed inner needle is introduced into a desired blood vessel, such as for example, the femoral artery or vein. The inner needle is then withdrawn and a coil spring wire guide is inserted through the lumen of the stylet into the blood vessel. External pressure is then applied to hold the wire guide in place while the stylet is withdrawn thereover. At this point the wire guide may either be manipulated to place the distal end in the desired body location and the catheter threaded over the wire guide to the selected area, or the catheter is threaded over the wire guide and pushed within 3 or 4 centimeters of the distal end of the wire guide, whereupon, using the wire guide as a leader, the wire guide and catheter are together advanced to the desired body location.

Anyone familiar with the body vascular system can easily appreciate that considerable manipulation is required to direct the wire guide or wire guide and catheter combination to the desired body location, due to the typically tortuous path involved. As a result, wire guides used for this purpose must be sufficiently flexible at the distal tip to permit negotiation of the desired path, yet also sufficiently rigid to resist undesirable bending or doubling back during insertion and withdrawal. Heretofore, these requirements have attempted to be met by constructing the wire guide of a closely wound coil spring having an inner opening which is solder-sealed at the proximal and distal ends. The inner opening includes a relatively stiff wire mandril which provides rigidity to the wire guide. Typically, the distal portion of the mandril terminates several centimeters short of the distal end of the wire guide. Wire guides of this type, however, exhibited problems because they were too flexible along the portion of the guide forward of the mandril and too rigid or stiff along the distal portion of the mandril.

The pertinent art dislcoses at least two types of wire guides which propose to solve the above noted problems. Wire guides of the first type provide a mandril having a taper along the distal portion so that there is a more gradual transition between the highly flexible distal tip of the wire guide and the relatively rigid non-tapered portion of the mandril. While an improvement, this type of wire guide still fails to provide the desired degree of flexibility and stiffness.

Another construction which is disclosed in catheter wire guides of the second type provides a mandril which is movable longitudinally within the opening of the wire guide. The movable mandril permits the stiffness of the distal portion of the wire guide to be varied by lengthening or shortening of the flexible portion of the wire guide. In actual use, however, movable mandrils have been found not to display the requisite ease of movement which is necessary for accurate control of the distal tip in the body.

The following patents are believed generally relevant to the apparatus of the present invention in that they disclose various designs for catheter wire guides:

| U.S. Pat. No. | Inventor |
|---|---|
| 3,452,740 | Muller |
| 3,612,058 | Ackerman |
| 3,437,103 | Cook |
| 3,789,841 | Antoshkiw |
| 4,080,706 | Heilman |
| 4,005,369 | Heilman |

U.S. Pat. No. 3,452,740 to Muller discloses a spring guide manipulator and wire guide therefor, the wire guide being an example of a helically wound wire guide with a flexible distal tip. The wire guide does not include a moveable mandril.

U.S. Pat. No. 3,612,058 to Ackerman discloses a further example of catheter stylet or wire guide having a helically wound wire and a tubular stiffening portion or mandril disposed axially along all but the distal most tip portion of the helically wound wire. The tubular stiffening portion is not axially movable in the wire guide.

U.S. Pat. No. 3,547,103 to Cook discloses an example of a coil spring wire guide for a catheter falling within the first type. The wire guide includes a tapered mandril which is soldered to the proximal end of the wire guide and terminates short of the distal end of the wire guide. The mandril is not longitudinally movable in the wire guide.

U.S. Pat. No. 3,789,841 to Antoshkiw discloses a disposable wire guide of the first type which includes a Teflon jacket coating the non-tapered portion of the core wire. The core wire is, however, not longitudinally movable within the wire guide.

U.S. Pat. No. 4,003,369 and U.S. Pat. No. 4,080,706 to Heilman et al. disclose a further example of a coil spring wire guide of the first type in which the coil spring wire is coated with Teflon prior to winding. These patents also do not disclose a movable mandril or core wire.

There exists a distinct need for a catheter wire guide having the requisite degree of flexibility and stiffness, yet which also avoids the disadvantages associated with previous designs for catheter wire guides.

SUMMARY OF THE INVENTION

A wire guide for guiding a catheter within a body blood vessel according to one embodiment of the present invention is characterized by a helically wound wire having an opening therethrough. There is further provided a mandril positioned within the opening and longitudinally movable therein relative to the helically wound wire for varying the flexibility of the distal tip of the wire guide. The wire guide is further characterized by a coating of lubricating material which coats the outer surface of the mandril and which facilitates smooth movement of the mandril within the opening of the wire guide.

Accordingly, it is an object of the present invention to provide an improved wire guide for guiding a catheter within a body blood vessel.

Further objects and advantages of the present invention will be made apparent by reference to the following figures and detailed description.

BRIEF DESCRIPTION OF THE DRAWINGS

FIG. 1 is a fragmentary sectional view of the wire guide of the present invention.

FIG. 1A is an enlarged fragmentary view, in full section, of the Teflon coated mandril of the present invention.

FIG. 2 is a fragmentary sectional view, similar to FIG. 1, of the wire guide of the present invention, but having the mandril withdrawn from the guide portion relative to the position shown in FIG. 1.

FIG. 3A is an enlarged fragmentary sectional view depicting the mandril without a bulb on the distal tip protruding through coils in the wire guide when an attempt is made to advance the mandril through a curved section of the wire guide.

FIG. 3B is an enlarged fragmentary sectional view similar to FIG. 3A, but with the mandril having a bulb on the distal tip and depicting how the mandril with the bulb is able to follow the curvature of the wire guide during advancement.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, there is illustrated the preferred embodiment of the wire guide of the present invention designated generally at 10. Wire guide 10 is seen to include a guide portion 11 and a handle portion 12 which are connected by a core wire or mandril 13 which is longitudinally movable within guide portion 11. Both guide portion 11 and handle portion 12 are formed of lengths of stainless steel helically wound wire 14 and 19, respectively. While not shown, it is to be understood that guide portion 11 may also be coated along its entire outer surface with a lubricating material such as Teflon in order to facilitate smooth movement of guide portion 11 within a body blood vessel and thereby minimize the hazards of blood clot generation and trauma to body tissues. The Teflon coating is preferably applied to guide portion 11 after wire 14 is helically wound so that the outer surface may be made more smooth than would be the case if the Teflon coating was applied prior to wire 14 being wound. This method of application also permits the Teflon coating to be applied only to the outer surface of guide portion 11 where it is needed, thereby resulting in a materials savings. The diameter of guide portion 11 will, of course, vary depending upon the size of the catheter to be placed in the body, which is itself dependent upon the size of the blood vessel or vessels to be catheterized, but will normally be within the range of from approximately 0.025 to 0.052 inches. A relatively small diameter (0.002 to 0.005") safety wire 15 having a circular cross-section extends between the proximal and distal tips 16 and 17, respectively, of guide portion 11 and is connected thereto by suitable means, such as a solder or weld. Alternatively, safety wire 15 may have a rectangular cross-section 0.002 to 0.004 inches thick and 0.006 to 0.012 inches wide. It may be appreciated that distal tip 17 is rounded to facilitate advancement of guide portion 11 within a body blood vessel, and the solder or weld at proximal tip 16 contains a passageway therethrough which is sized to allow longitudinal movement of mandril 13 within guide portion 11. Mandril 13 is disposed within the longitudinal opening 18 defined by the inner surface of guide portion 11 and is longitudinally moveable therein by external manipulation of handle portion 12 in a manner which will be fully described later herein.

The proximal most portion of mandril 13 is received and securely anchored at ends 20 and 21 of handle portion 12 by a solder or weld. Wire 19 is made from stainless steel and may have a diameter which corresponds to the diameter of wire 14. Mandril 13 is formed from a length of stainless steel wire 13A having a diameter in a range from 0.012 to 0.021 inches and has a tapered distal portion 23 which narrows towards an enlargement or bulb 23A at the distal tip of mandril 13. Tapering of distal portion 23 serves to permit a gradual transition in flexibility from the highly flexible portion of guide portion 11 ahead of tip 23 to the relatively much stiffer portion of guide portion 11 coextensive with the nontapered portion of mandril 13.

Bulb 23A allows mandril 13 to follow around curves in coil spring 14 when it is advanced. As seen in FIG. 3A, without bulb 23A the tapered end of mandril 13 would lodge in the space between the coils of wire 14 and actually protrude outside the coils if it is advanced further. This would cause considerable trauma to a blood vessel. As clearly seen in FIG. 3B, bulb 23A has a relatively short length so that it does not appreciably affect the stiffness of the coil and has a diameter which is sufficiently large to prevent mandril 13 from exiting between the coils and protruding into a blood vessel. Preferably, the diameter of bulb 23A is approximately equal to the diameter of the untapered portion of mandril 13 and a length which is 2–5 times this diameter.

Mandril 13 is coated with a layer 24 of lubricating material, such as Teflon, which serves to facilitate the smooth movement of mandril 13 within longitudinal opening 18. It is to be appreciated that mandril 13 provides the necessary stiffness and rigidity to guide portion 11 to permit it to be advanced through a typically tortuous path in the vascular system. It must also be appreciated that the distal most portion of guide portion 11 must be sufficiently flexible to permit guide portion 11 to negotiate relatively sharp bends or turns, such as is for example encountered when guide portion 11 is advanced through a side passage of a blood vessel which is branched from the main passage. In order to provide flexibility to the distal most portion of guide portion 11, mandril 13 is positioned so as to terminate several centimeters behind distal tip 17 of guide portion 11. This condition is depicted in FIG. 2. The relative amount of flexibility at distal tip 17 may be varied therefrom as required during advancement of the wire guide into a desired body location by positioning the distal end of mandril 13 closer to or further apart from distal tip 17. FIG. 1 shows the distal end of mandril 13 positioned relatively closer to distal tip 17, such as would be accomplished when it is necessary to increase the stiffness of the distal portion of the wire guide.

Relative movement of mandril 13 within guide portion 11 is accomplished by external manipulation of mandril 13 in the following manner. The proximal portion of guide portion 11 is grasped with the thumb and forefinger of one hand and held in position and handle portion 12 is grasped with the thumb and forefinger of the other hand and moved towards or away from guide portion 11 by a pushing or pulling movement on handle portion 12. The use of a Teflon coating on mandril 13 permits smooth movement of mandril 13 within opening 18 despite the tortuous path negotiated by guide portion 11 and the presence of safety wire 15 which may otherwise substantially inhibit longitudinal movement. Further, the use of a tapered tip on mandril 13 ensures a gradual transition in the degree of flexibility.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A wire guide having a flexible distal tip and adapted for guiding a catheter within a body blood vessel, comprising:
    a helically wound wire including coils defining a longitudinal opening;
    a mandril including distal and proximal ends and having a distal portion and a proximal portion, said mandril being slidably received within said longitudinal opening of said wire, whereby said distal end of said mandril is longitudinally movable therein relative to said wire for varying the flexibility of said distal tip of said wire guide, said distal portion being tapered inwardly towards the distal end of said mandril thereby causing said wire guide flexibility to progressively increase along said taper, said mandril further including an enlarged bulb at said distal end, whereby said bulb permits said mandril to be advanced relative to the longitudinal opening of said helically wound wire with the flexible distal tip of said wire guide flexed without said mandril protruding through the coils of said helically wound wire; and,
    a means, including a coating of lubricating material, for facilitating smooth movement of said mandril within said opening of said helically wound wire.

2. The apparatus of claim 1 wherein said coating of lubricating material coats the outer surface of said mandril.

3. The apparatus of claim 1 wherein the proximal portion of said mandril is untapered and has a diameter and said bulb has a diameter approximately equal to the diameter of the untapered portion of said mandril and a length which is 2–5 times said mandril diameter.

4. The apparatus of claim 3 wherein said helically wound wire is coated on its outer surface with a lubricating material, said lubricating material facilitating smooth movement of said wire guide through said blood vessel.

5. The apparatus of claim 2 wherein said lubricating material is Teflon.

* * * * *